(12) United States Patent
Brookfield et al.

(10) Patent No.: US 7,879,884 B2
(45) Date of Patent: Feb. 1, 2011

(54) ARYL PYRIDYL SULFONAMIDE DERIVATIVES, THEIR MANUFACTURE AND USE AS PHARMACEUTICAL AGENTS

(75) Inventors: Frederick Brookfield, Wallingford (GB); Lothar Kling, Mannheim (DE); Ulrike Reiff, Penzberg (DE); Wolfgang Von der Saal, Murnau (DE); Thomas Von Hirschheydt, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/599,699

(22) PCT Filed: May 14, 2008

(86) PCT No.: PCT/EP2008/003852

§ 371 (c)(1),
(2), (4) Date: Nov. 11, 2009

(87) PCT Pub. No.: WO2008/138594

PCT Pub. Date: Nov. 20, 2008

(65) Prior Publication Data

US 2010/0256200 A1 Oct. 7, 2010

(30) Foreign Application Priority Data

May 16, 2007 (EP) .................... 07009761

(51) Int. Cl.
*A61K 31/44* (2006.01)
*C07D 213/00* (2006.01)
(52) U.S. Cl. ........................ 514/351; 546/293
(58) Field of Classification Search ............... 546/293; 514/351
See application file for complete search history.

(56) References Cited

U.S. PATENT DOCUMENTS 4,018,929 A 4/1977 Delarge et al.

2006/0270874 A1 11/2006 Boyd et al.
2007/0010564 A1 1/2007 Boyd et al.

FOREIGN PATENT DOCUMENTS

| WO | WO 02/24636 | 3/2002 |
| WO | WO 02/098848 | 12/2002 |
| WO | WO 03/029217 | 4/2003 |
| WO | WO 03/035629 | 5/2003 |
| WO | WO 2004/048329 | 6/2004 |

OTHER PUBLICATIONS

Hcaplus 2004:773118, "Acyl Sulfonamide Anti-Proliferatives. Benzene Substituent Structure-Activity Relationships for a Novel Class of Antitumor Agents", Lobb et. al., 2004.*
Delarge et al., Annales Pharma. Francaises vol. 41 (1983) pp. 55-60.
Owa et al., Bioorg. Med. Chem. Lett. (2002) vol. 12(16) pp. 2097-2100.

* cited by examiner

*Primary Examiner*—Janet L Andres
*Assistant Examiner*—Binta M Robinson
(74) *Attorney, Agent, or Firm*—George W. Johnston; Patricia S. Rocha-Tramaloni; David E. Wildman

(57) ABSTRACT

Objects of the present invention are the compounds of formula (I) their pharmaceutically acceptable salts, enantiomeric forms, diastereoisomers and racemates, the preparation of the above compounds, medicaments containing them and their manufacture, as well as the use of the above compounds in the control or prevention of illnesses such as cancer.

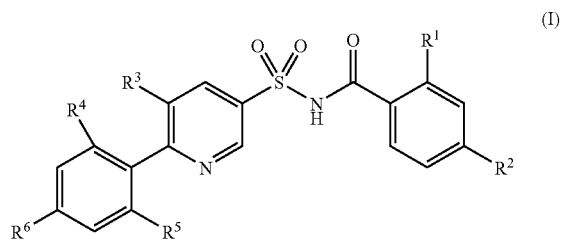

(I)

5 Claims, No Drawings

ARYL PYRIDYL SULFONAMIDE DERIVATIVES, THEIR MANUFACTURE AND USE AS PHARMACEUTICAL AGENTS

This application is the national stage of International Application No. PCT/EP2008/003852, filed May 14, 2008, which claims the benefit of European Application No. 07009761.3, filed May 16, 2007, which is hereby incorporated by reference in its entirety.

The present invention relates to novel aryl pyridyl sulfonamide derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy.

The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

Delarge, J., et al, Annales Pharmaceutiques Francaises 41 (1983) 55-60, describes some 4-phenylthiopyridine-3-sulfonamides with hypolipemic properties. U.S. Pat. No. 4,018,929 relates to pyridinesulfonamides as inflammation inhibitors and diuretics. Owa, T., et al, Bioorg Med Chem Lett (2002), 12(16), 2097-2100 relates to N-(7-indolyl)-3-pyridinesulfonamide derivatives as antitumor agents. WO 2003/029217 relates to new pyridinic sulfonamide derivatives an their use as therapeutic agents in the treatment of inflammation, arthrosis, cancer, angiogenesis and asthma WO 2003/035629 relates to thiophene- and thiazolesulfonamides as antineoplastic agents. WO 02/098848 and WO 2004/048329 relate to benzoylsulfonamides as antitumor agents. US 2006270874 describes styrylsulfonamides as anticancer agents and their preparation. US 2007010564 relates to the preparation of heteroarylethenesulfonic acid N-benzoylamide derivatives as anticancer agents.

SUMMARY OF THE INVENTION

The present invention relates to heterocyclyl pyridyl sulfonamides of the general formula I

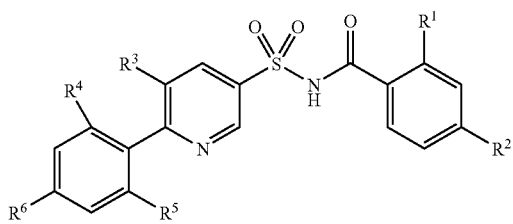

formula I wherein
$R^1$ is chlorine, bromine, methyl, methoxy or trifluoromethyl;
$R^2$ is fluorine, chlorine, bromine, methyl or trifluoromethyl;
$R^3$ is hydrogen or methyl;
$R^4$ is alkoxy, alkyl, alkylsulfanyl, halogen, trifluoromethyl, trifluoromethoxy, —S(O)$_2$CH$_3$ or —NH—S(O)$_2$CH$_3$;
$R^5$ is hydrogen, alkoxy, alkyl, halogen, trifluoromethyl or trifluoromethoxy;
$R^6$ is hydrogen, alkyl or trifluoromethyl;
and all pharmaceutically acceptable salts thereof.

The compounds according to this invention show antiproliferative activity and inhibit the growth of tumor cells in vitro and in vivo. Objects of the present invention are the compounds of formula I and their tautomers, pharmaceutically acceptable salts, enantiomeric forms, diastereoisomers and racemates, their use for the inhibition of tumor growth, the preparation of the above-mentioned compounds, medicaments containing them and their manufacture as well as the use of the above-mentioned compounds in the control or prevention of illnesses, especially of cancers such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

DETAILED DESCRIPTION OF THE INVENTION

1. Definitions

The term "alkyl" as used herein means a saturated, straight-chain or branched-chain hydrocarbon containing from 1 to 4 carbon atoms, preferably 1 to 3 carbon atoms and more preferably 1 to 3 carbon atoms, such as methyl, ethyl, n-propyl, isopropyl, n-butyl, 2-butyl or t-butyl, preferably methyl.

The term "alkoxy" as used herein refers to an alkyl group as defined above which attached via an oxygen atom (alkyl-O—), such as methoxy, ethoxy or isopropoxy, preferably methoxy.

The term "alkylsulfanyl" as used herein refers to an alkyl group as defined above which attached via an sulfur atom (alkyl-S—), such as methylsulfanyl, ethylsulfonyl or isopropylsulfanyl, preferably methylsulfanyl.

The term "halogen" as used herein means fluorine, chlorine and bromine, preferably fluorine or chlorine.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

2. Detailed Description $R^1$ is chlorine, bromine, methyl, methoxy or trifluoromethyl; preferably chlorine, methoxy or trifluoromethyl.

$R^2$ is fluorine, chlorine, bromine, methyl or trifluoromethyl; preferably fluorine or chlorine.

$R^3$ is hydrogen or methyl; preferably hydrogen.

$R^4$ is alkoxy, alkyl, alkylsulfanyl, halogen, trifluoromethyl, trifluoromethoxy, —S(O)$_2$CH$_3$ or —NH—S(O)$_2$CH$_3$; preferably methoxy, methyl, methylsulfanyl, chlorine, trifluoromethyl, —S(O)$_2$CH$_3$ or —NH—S(O)$_2$CH$_3$;

$R^5$ is hydrogen, alkoxy, alkyl, halogen, trifluoromethyl or trifluoromethoxy; preferably hydrogen, methoxy, methyl or fluorine.

$R^6$ is hydrogen, alkyl or trifluoromethyl, preferably hydrogen, methyl, or trifluoromethyl; and more preferably hydrogen.

One embodiment of the invention are the compounds of formula I, wherein $R^1$ is chlorine.

Another embodiment of the invention are the compounds of formula I, wherein $R^1$ is chlorine; and $R^2$ is fluorine or chlorine.

Another embodiment of the invention are the compounds of formula I, wherein $R^1$ is chlorine; and $R^2$ is fluorine.

Such compounds, for example, may be selected from the group consisting of 6-(2-Chloro-phenyl)-5-methyl-pyridine-3-sulfonic acid 2-chloro-4-fluoro-benzoylamide; potassium salt;

6-(2,6-Dimethoxy-phenyl)-pyridine-3-sulfonic acid 2-chloro-4-fluoro-benzoylamide.

Another embodiment of the invention are the compounds of formula I, wherein $R^1$ is chlorine; and $R^2$ is chlorine.

Such compounds, for example, may be selected from the group consisting of 6-(2-Methoxy-phenyl)-5-methyl-pyridine-3-sulfonic acid 2,4-dichloro-benzoylamide; potassium salt;

6-(2-Fluoro-6-methoxy-phenyl)-pyridine-3-sulfonic acid 2,4-dichloro-benzoylamide; potassium salt;

6-(2,4-Bis-trifluoromethyl-phenyl)-pyridine-3-sulfonic acid 2,4-dichloro-benzoylamide; potassium salt;

6-(2-Methylsulfanyl-phenyl)-pyridine-3-sulfonic acid 2,4-dichloro-benzoylamide; potassium salt;

6-(2,6-Dimethoxy-phenyl)-pyridine-3-sulfonic acid 2,4-dichloro-benzoylamide; and 6-(2-Methanesulfonyl-phenyl)-pyridine-3-sulfonic acid 2,4-dichloro-benzoylamide; potassium salt.

Another embodiment of the invention are the compounds of formula I, wherein $R^1$ is methoxy.

Another embodiment of the invention are the compounds of formula I, wherein $R^1$ is methoxy; and $R^2$ is chlorine.

Such compounds, for example, may be selected from the group consisting of:

6-(2-Chloro-phenyl)-5-methyl-pyridine-3-sulfonic acid 4-chloro-2-methoxy-benzoylamide; potassium salt;

6-(2-Methanesulfonylamino-phenyl)-pyridine-3-sulfonic acid 4-chloro-2-methoxy-benzoylamide; potassium salt;

6-(2,6-Dimethyl-phenyl)-pyridine-3-sulfonic acid 4-chloro-2-methoxy-benzoylamide; potassium salt;

6-(2,4,6-Trimethyl-phenyl)-pyridine-3-sulfonic acid 4-chloro-2-methoxy-benzoylamide; potassium salt; and 6-(2,6-Dimethoxy-phenyl)-pyridine-3-sulfonic acid 4-chloro-2-methoxy-benzoylamide; potassium salt.

Another embodiment of the invention are the compounds of formula I, wherein $R^1$ is trifluoromethyl.

Another embodiment of the invention are the compounds of formula I, wherein $R^1$ is trifluoromethyl; and $R^2$ is fluorine.

Such compounds, for example, may be selected from the group consisting of 6-(2-Chloro-phenyl)-5-methyl-pyridine-3-sulfonic acid 4-fluoro-2-trifluoromethyl-benzoylamide; potassium salt;

6-(2-Methoxy-phenyl)-5-methyl-pyridine-3-sulfonic acid 4-fluoro-2-trifluoromethyl-benzoylamide; potassium salt; and 6-(2,6-Dimethoxy-phenyl)-pyridine-3-sulfonic acid 4-fluoro-2-trifluoromethyl-benzoylamide.

Another embodiment of the invention are the compounds of formula I, wherein $R^3$ is hydrogen.

Another embodiment of the invention are the compounds of formula I, wherein $R^3$ is methyl.

Another embodiment of the invention are the compounds of formula I, wherein $R^4$ is methoxy, methyl, methylsulfanyl, chlorine, trifluoromethyl, —S(O)$_2$CH$_3$ or —NH—S(O)$_2$CH$_3$;

$R^5$ is hydrogen, methoxy, methyl or fluorine; and $R^6$ is hydrogen, methyl or trifluoromethyl.

Another embodiment of the invention are the compounds of formula I, wherein $R^1$ is chlorine, methoxy or trifluoromethyl;

$R^2$ is fluorine or chlorine;

$R^4$ is methoxy, methyl, methylsulfanyl, chlorine, trifluoromethyl, —S(O)$_2$CH$_3$ or —NH—S(O)$_2$CH$_3$;

$R^5$ is hydrogen, methoxy, methyl or fluorine; and $R^6$ is hydrogen, methyl or trifluoromethyl.

Another embodiment of the invention are the compounds of formula I, wherein $R^1$ is chlorine, methoxy or trifluoromethyl $R^2$ is fluorine or chlorine; and $R^4$ is methoxy, methyl, methylsulfanyl, chlorine, trifluoromethyl, —S(O)$_2$CH$_3$ or —NH—S(O)$_2$CH$_3$.

Another embodiment of the invention are the compounds of formula I, wherein
- $R^1$ is chlorine, methoxy or trifluoromethyl
- $R^2$ is fluorine or chlorine; and
- $R^4$ is methoxy, methylsulfanyl, chlorine, —S(O)$_2$CH$_3$ or —NH—S(O)$_2$CH$_3$.
- $R^5$ is hydrogen; and
- $R^6$ is hydrogen.

Another embodiment of the invention are the compounds of formula I, wherein
- $R^1$ is chlorine, methoxy or trifluoromethyl
- $R^2$ is fluorine or chlorine;
- $R^4$ is methoxy or methyl;
- $R^5$ is methoxy, methyl or fluorine; and
- $R^6$ is hydrogen or methyl.

Another embodiment of the invention are the compounds of formula I, wherein
- $R^1$ is chlorine, methoxy or trifluoromethyl
- $R^2$ is fluorine or chlorine;
- $R^4$ is trifluoromethyl;
- $R^5$ is hydrogen;
- $R^6$ is methyl or trifluoromethyl.

Another embodiment of the invention are the compounds of formula I, wherein
- $R^1$ is chlorine, methoxy or trifluoromethyl
- $R^2$ is fluorine or chlorine; and
- $R^5$ is hydrogen, methoxy, methyl or fluorine.

Another embodiment of the invention are the compounds of formula I, wherein
- $R^1$ is chlorine, methoxy or trifluoromethyl
- $R^2$ is fluorine or chlorine; and
- $R^6$ is hydrogen, methyl or trifluoromethyl.

One embodiment of the invention is a process for the preparation of the compounds of formula I, by
reacting a compound of formula V,

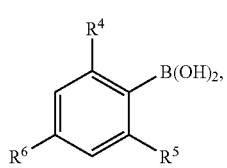

formula V wherein $R^4$, $R^5$ and $R^6$ have the significance given for formula I, with a compound of formula IV,

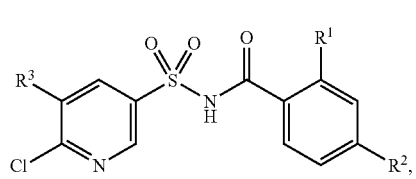

formula IV wherein $R^1$, $R^2$ and $R^3$ have the significance given for formula I, to give the compounds of formula I,

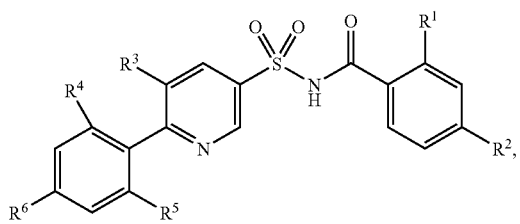

formula I wherein $R^1$, $R^2$, $R^3$, $R^4$, $R^5$ and $R^6$ have the significance given for formula I.

The compounds of formula I, or a pharmaceutically acceptable salt thereof, which are subject of the present invention, may be prepared by any process known to be applicable to the preparation of chemically-related compounds. Such processes, when used to prepare a compound of the formula I, or a pharmaceutically-acceptable salt thereof, are illustrated by the following representative schemes 1 and 2 (and the examples) in which, unless otherwise stated, $R^1$ to $R^6$ have the significance given herein before for formula I. Necessary starting materials are either commercially available or they may be obtained by standard procedures of organic chemistry. The preparation of such starting materials is e.g. described within the accompanying examples or in the literature cited below with respect to scheme 1 and 2. Alternatively necessary starting materials are obtainable by analogous procedures to those illustrated which are within the ordinary skill of an organic chemist.

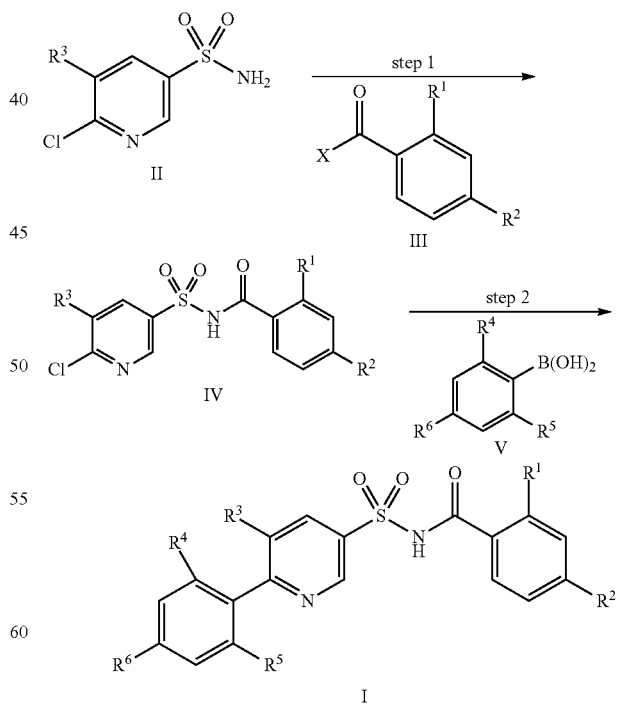

Step 1 of the reaction sequence (scheme 1) is a one step process in which acylation with a benzoyl derivative of formula III of the sulfonamide of formula II gives the acylsulfonamide derivatives of formula IV using methods well known to someone skilled in the art. The reaction is typically carried out in solvents such as dichloromethane, dichloroethane, acetonitrile, dioxane, tetrahydrofuran, chloroform, dimethylformamide and mixtures thereof, at temperatures between 10° C. and 100° C. Typically used bases are sodium hydride, potassium hydride, potassium carbonate, triethylamine, diisopropylethylamine, and 1,8-diazabicyclo[5.4.0]undec-7-ene.

Step 2 of the reaction sequence is a Suzuki-type palladium-catalyzed cross coupling of a phenylboronic acid of formula V with the 2-chloropyridines of formula IV well known to someone skilled in the art. The reaction is typically carried out in solvents such as alcohols (e.g. ethanol, iso-propanol, n-butanol, t-amyl-alcohol), tetrahydrofurane or toluene and mixtures thereof, at temperatures typically between room temperature and 120° C. Commonly used bases are the carbonates of potassium and sodium, potassium tert-butylat and potassium hydroxide. Ligands for the palladium catalysts are legion by know, well described in the literature. Most frequently used is triphenylphosphine and dibenzylideneacetone (dba).

Alternatively the sequence of substitution can be varied as shown in scheme 2:

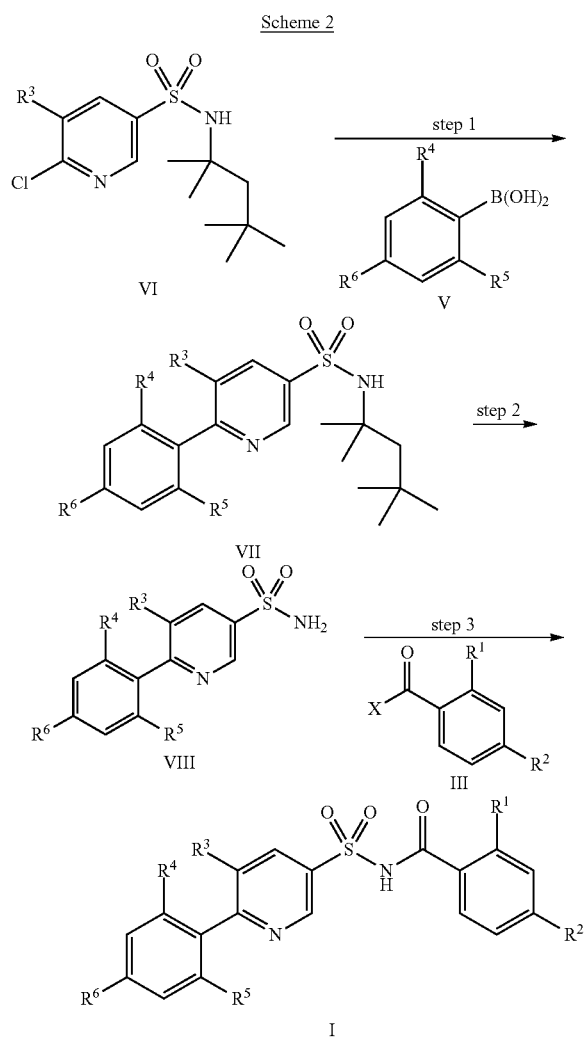

Starting from a tert-octyl-protected sulfonamide of formula VI a Suzuki-type cross coupling as described for step 2 in scheme 1 is performed prior to the deprotection of the sulfonamide under acidic conditions using trifluoroacetic acid in dichloromethane and the acylation step as described for step 1 in scheme 1.

The compounds of formula I can contain one or several chiral centers and can then be present in a racemic, a enantiomeric or diastereomeric form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmaceutical composition or medicaments containing a compound of the present invention or a pharmaceutically acceptable salt thereof and a pharmaceutically acceptable carrier are an object of the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

An embodiment of the invention is a pharmaceutical composition, containing one or more compounds according to formula I, together with pharmaceutically acceptable carriers.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a pharmaceutical composition containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of cancer.

Another embodiment of the invention is the use of the compounds of formula I as anti-proliferating agents.

Another embodiment of the invention is the use of one or more compounds of formula I for the treatment of cancer.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or, if the compounds of formula I contain a basic group in R1, from organic or inorganic acids. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

Pharmacological Activity

The compounds of formula I and their pharmaceutically acceptable salts possess valuable pharmacological properties. It has been found that said compounds show anti-proliferative activity. Consequently the compounds of the present invention are useful in the therapy and/or prevention of proliferative diseases such as cancer. The activity of the present compounds as anti-proliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCI-247) were cultivated in RPMI 1640 medium with GlutaMAX™ I (Invitrogen, Cat-No. 61870-010), 5% Fetal Calf Serum (FCS, Sigma Cat-No. F4135 (FBS)); 100 Units/ml penicillin/104%/ml streptomycin (=Pen/Strep from Invitrogen Cat. No. 15140).

For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:
Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
HCT116 (ATCC-No. CCI-247): 1000 cells in 60 µl per well of 384 well plate (Greiner 781098, µClear-plate white)
After seeding incubate plates 24 h at 37° C., 5% $CO_2$ 2nd. day: Induction (Treatment with Compounds, 10 Concentrations):
In order to achieve a final concentration of 30 µM as highest concentration 3.5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a -e) as described here below:

a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1: 47.6 (3.5 µl compound dilution to 163 µl media)
e) add 10 µl of every concentration to 60 µl media in the cell plate resulting in final concentration of DMSO: 0.3% in every well and resulting in 10 final concentration of compounds ranging from 30 µM to 0.0015 µM.
Each compound is tested in triplicate.
Incubate 120 h (5 days) at 37° C., 5% $CO_2$ Analysis:
Add 30 µl CellTiter-Glo™ Reagent per well,
shake 15 minutes at room temperature
incubate further 45 minutes at room temperature without shaking Measurement:
Victor 2 scanning multiwell spectrophotometer (Wallac), Luminescence mode (0.5 sec/read, 477 nm)
Determine IC50 using a non-linear curve fit (XLfit software (ID Business Solution Ltd., Guilford, Surrey, UK))

With all compounds a significant inhibition of HCT 116 cell viability was detected, which is exemplified by the compounds shown in Table 1.

TABLE 1

| Results: | |
| --- | --- |
| Examples | IC50 HCT 116 [µM] |
| 1-1 | 1.433 |
| 1-8 | 2.936 |
| 1-12 | 3.985 |
| 1-2, 1-3, 1-4, 1-5, 1-6, 1-7, 1-9, 1-10, 1-11, -1-13, 1-14, 1-15, 1-16 | 0.500-7.500 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically acceptable, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:

| a) Tablet Formulation (Wet Granulation): | | | | |
|---|---|---|---|---|
| Item | Ingredients | | mg/tablet | | |
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| b) Capsule Formulation: | | | | |
|---|---|---|---|---|
| Item | Ingredients | | mg/capsule | | |
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples are provided to aid the understanding of the present invention, the true scope of which is set forth in the appended claims. It is understood that modifications can be made in the procedures set forth without departing from the spirit of the invention.

EXPERIMENTAL PROCEDURES

6-Chloro-pyridine-3-sulfonyl chloride

Sodium nitrite (3.45 g, 0.05 mol) was added portion wise to a stirred solution of 6-chloro-pyridin-3-ylamine (6.4 g, 0.05 mol) in acetic acid (56 ml) and HCl (conc) (9.92 ml) while maintaining the temperature below 15° C. This solution was then added drop wise to a stirred solution of sulfur dioxide (17.2 g, 0.27 mol), copper (II) chloride (1.85 g, 0.011 mol) and water (2.2 ml) in acetic acid (37 ml) at 5° C. The reaction mixture was allowed to warm to room temperature and poured over ice water and stirred for a further 15 min. The resultant precipitate was collected by filtration, washed with water and dried overnight in a vacuum oven to give 6-chloro-pyridine-3-sulfonyl chloride (6.41 g, 60.5% yield); (400 MHz; $d^6$-DMSO) 8.54 (1H, d), 7.96 (1H, dd), 7.50 (1H, d).

6-Chloro-pyridine-3-sulfonic acid amide

6-Chloro-pyridine-3-sulfonyl chloride (5.0 g, 0.024 mol) was dissolved in a 0.5M solution of ammonia in dioxane (125 mL) at −5° C. The mixture was allowed to warm to room temperature and the mixture stirred for 1 hour. The mixture was filtered through celite, washed twice with dioxane and concentrated in vacuo to afford 6-choro-pyridine-3-sulfonic acid amide as an off white solid 4.55 g (98% yield). LC@UV215 nm; Rt 1.05: 100%, m/z (ES+): 193/195 (400 MHz; $d^6$-DMSO) 8.79 (1H, d), 8.21 (1H, dd), 7.75 (1H, d) 7.70 (2H, br S).

6-Chloro-pyridine-3-sulfonic acid 2,4-dichloro-benzoyl amide 1,1'-Carbonyl-diimidazole (4.22 g, 26 mmol) was added to a solution of 2,4-dichlorobenzoic acid (4.73 g, 24.8 mmol) in 100 ml dichloromethane the mixture was stirred for 30 minutes at room temperature and subsequently refluxed for 30 minutes. Then 6-chloro-pyridine-3-sulfonic acid amide (5.00 g, 26 mmol) and 1,8-diazabicylo[5.4.0]undec-7-en (3.96 g, 26 mmol) were added and the mixture was stirred at room temperature overnight. After evaporation to dryness the residue was taken up with 100 ml ethyl acetate and washed with 1 M HCl and 1 M NaOH and the organic phase was dried over sodium sulphate and concentrated in vacuo. Flash chromatography ($SiO_2$, heptane-ethyl acetate gradient) yielded 6.72 g of the title compound as a white solid, m/z=365 (ES+), 363 (ES−).

6-Chloro-pyridine-3-sulfonic acid (1,1,3,3-tetramethyl-butyl)-amide

6-Chloro-pyridine-3-sulfonyl chloride (148.0 g, 0.7 mol) was suspended in 1000 ml dry dichloromethane and added in portions over 45 minutes to a solution of 1,1,3,3-tetramethylbutylamine (465 ml 2.8 mol) and triethylamine (195 ml, 1.4 mol) in 2800 ml dry dichloromethane, keeping the temperature between −40° C. and −30° C. After addition the mixture was allowed to warm up to room temperature and stirred for an additional hour. The reaction mixture was washed three times with 1 M HCl (2000 ml each time) and twice with water (1000 ml each time). The organic layer was dried over sodium sulphate and evaporated to dryness. The residue was triturated with iso-hexane and filtered off and dried in vacuo at 40° C. to yield 90 g of the title compound.

6-(2,6-Dimethoxy-phenyl)-pyridine-3-sulfonic acid (1,1,3,3-tetramethyl-butyl)-amide 2,6-dimethoxyphenylboronic acid (1.0 g, 5.5 mmol), 6-Chloro-pyridine-3-sulfonic acid (1,1,3,3-tetramethyl-butyl)-amide (555 mg, 1.8 mmol) and potassium carbonate (1.0 g, 7.3 mmol) were added to a degassed solution of tetrakis (triphenylphosphine) palladium (404 mg, 0.35 mmol) in toluol (12 ml) and ethanol (6 ml) and heated in a microwave reactor for 90 minutes at 90° C. The mixture was evaporated to dryness, suspended in 50 methanol and filtered off. The filtrate was evaporated to dryness and the residue was purified by flash chromatography ($SiO_2$, heptane-ethyl acetate gradient) to return 639 mg of the title compound as an off-white solid, m/z=407 (ES+), 405 (ES−).

6-(2,6-Dimethoxy-phenyl)-pyridine-3-sulfonic acid amide

Trifluoroacetic acid (3.6 ml, 47 mmol) was added to a solution of 6-(2,6-Dimethoxy-phenyl)-pyridine-3-sulfonic acid (1,1,3,3-tetramethyl-butyl)-amide (1.90 g, 4.7 mmol) in 40 ml dichloromethane and stirred at room temperature (monitored by TLC). The mixture was evaporated to dryness, taken up in 10 ml ethyl acetate and washed with aqueous sodium bicarbonate. The organic layer was evaporated to dryness and the residue was purified by flash chromatography ($SiO_2$, heptane-ethyl acetate gradient) to return 1.28 g of the title compound as an off-white solid, m/z=295 (ES+), 293 (ES−).

6-Chloro-5-methyl-pyridine-3-sulfonic acid 2,4-dichloro-benzoylamide

NaH (2.0 g, 84.9 mmol, 60% suspension in mineral oil) was added to THF (50 ml) and stirred for 15 min. To this suspension was added a solution of 6-chloro-5-methyl-pyridine-3-sulfonic acid amide (preparation described e.g. in U.S. Pat. No. 3,718,654) (7.0 g, 33 mmol) in THF (50 ml) at 0° C. and the reaction mixture was allowed to warm to room temperature and stirred for 30 min. To this mixture was added the 2,4-dichlorobenzoyl chloride [A mixture of 2,4-dichlorobenzoic acid (9.73 g, 50.9 mmol), toluene (200 ml) and $SOCl_2$ (10 ml, 135 mmol) was refluxed for 3 h. The reaction mixture was cooled to RT, concentrated and diluted with dry THF (100 ml)] at 0° C. and stirred at RT for 15 min. The reaction mixture was quenched with saturated $NH_4Cl$ solution (100 ml), concentrated and extracted with ethyl acetate. The combined organics was washed with saturated $NaHCO_3$, brine, dried, evaporated and purified by crystallization from methanol to get 6.5 g (51%) of 7 as off white solid. $^1H$ NMR (400 MHz, DMSO-$d_6$): δ 2.30 (s, 1H), 7.31 (d, J=8.6 Hz, 1H), 7.46-7.49 (m, 2H), 8.12 (s, 1H), 8.56 (s, 1H). FIA-MS: (m/z 379).

Final Products

Sodium or Potassium Salt Formation

Depending on the synthetic route and the work-up procedure i.e. the HPLC purification conditions, the final products described below (in Examples 1-1 to 1-16) were obtained either as sulfonamide potassium salts (neutral HPLC-conditions—e.g. aqueous eluent is water (pH is 7)/acetonitrile 9:1 and the organic eluent is acetonitrile) or they were obtained as sulfonamides in their salt free form (route 2, acidic HPLC conditions—e.g. the aqueous eluent is water with 0.2% acetic acid and the organic eluent is acetonitrile with 0.2% acetic acid)

These obtained sulfonamides or sulfonamide potassium salts were or are converted to their sodium salts using the following procedure:

To a solution of the sulfonamide (1 eq., e.g. 1 mmol) in tetrahydrofuran (e.g. 10 ml), 1 eq. (e.g. 1 mmol) sodium methoxide (25% solution in methanol) is added and the mixture is stirred at room temperature for 1 hour. The tetrahydrofuran is removed in vacuo and the residue suspended in diethyl ether (e.g. 50 to 100 ml) and heated to reflux four 1 hour, cooled down to room temperature filtered off and dried.

Example 1-1

6-(2,6-Dimethoxy-phenyl)-pyridine-3-sulfonic acid 2,4-dichloro-benzoylamide (and its Sodium Salt)

2,6-dimethoxyphenylboronic acid (286 mg, 1.6 mmol), 6-Chloro-pyridine-3-sulfonic acid 2,4-dichloro-benzoyl amide (190 mg, 0.5 mmol) and potassium carbonate (290 mg, 2.1 mmol) were added to a degassed solution of tetrakis (triphenylphosphine) palladium (116 mg, 0.1 mmol) in toluol (3.3 ml) and ethanol (1.7 ml) and heated in a microwave reactor for 90 minutes at 90° C. The mixture was evaporated to dryness, suspended in 1.5 ml of a 1:1:1 mixture of acetonitrile, water and methanol and filtered off. The filtrate was evaporated to dryness and the residue was purified by flash chromatography ($SiO_2$, heptane-ethyl acetate gradient) to return 133 mg of the title compound as a light solid, m/z=467 (ES+), 465 (ES−).

The reaction with sodium methoxide in THF was carried out as described above to give the corresponding sodium salt.

Example 1-2

6-(2,6-Dimethoxy-phenyl)-pyridine-3-sulfonic acid 2-chloro-4-fluoro-benzoylamide and its Sodium Salt 1,1'-Carbonyl-diimidazole (60 mg, 0.4 mmol) was added to a solution of 2-chloro-4-fluorobenzoic acid (56 mg, 0.3 mmol) in 10 ml dichloromethane the mixture was refluxed for 30 minutes. Then 6-(2,6-Dimethoxy-phenyl)-pyridine-3-sulfonic acid amide (100 mg, 0.3 mmol) and 1,8-diazabicylo [5.4.0]undec-7-en (56 mg, 0.4 mmol) were added and the mixture was stirred at room temperature overnight. After evaporation to dryness the residue was purified by preparative HPLC/MS (RP18, methanol-water-gradient containing 1% acetic acid) to yield 107 mg of the title compound as a white solid, m/z=451 (ES+), 449 (ES−).

The reaction with sodium methoxide in THF was carried out as described above to give the corresponding sodium salt.

Example 1-3 to 1-16

The following examples were prepared in an analogous manner as described for example 1-1 or 1-2, respectively, using the appropriate starting material:

| Example No. | Systematic Name | MS (ES+) |
|---|---|---|
| 1-3 | 6-(2,6-Dimethoxy-phenyl)-pyridine-3-sulfonic acid 4-fluoro-2-trifluoromethyl-benzoylamide | 485 |
| 1-4 | 6-(2,6-Dimethoxy-phenyl)-pyridine-3-sulfonic acid 4-chloro-2-methoxy-benzoylamide; potassium salt | 463 |
| 1-5 | 6-(2,4,6-Trimethyl-phenyl)-pyridine-3-sulfonic acid 4-chloro-2-methoxy-benzoylamide | 445 |
| 1-6 | 6-(2,6-Dimethyl-phenyl)-pyridine-3-sulfonic acid 4-chloro-2-methoxy-benzoylamide; potassium salt | 431 |
| 1-7 | 6-(2-Methylsulfanyl-phenyl)-pyridine-3-sulfonic acid 2,4-dichloro-benzoylamide; potassium salt | 453 |
| 1-8 | 6-(2-Methanesulfonyl-phenyl)-pyridine-3-sulfonic acid 2,4-dichloro-benzoylamide; potassium salt | 485 |

-continued

| Example No. | Systematic Name | MS (ES+) |
| --- | --- | --- |
| 1-9 | 6-(2,4-Bis-trifluoromethyl-phenyl)-pyridine-3-sulfonic acid 2,4-dichloro-benzoylamide; potassium salt | 543 |
| 1-10 | 6-(2-Fluoro-6-methoxy-phenyl)-pyridine-3-sulfonic acid 2,4-dichloro-benzoylamide; potassium salt | 455 |
| 1-11 | 6-(2-Methanesulfonylamino-phenyl)-pyridine-3-sulfonic acid 4-chloro-2-methoxy-benzoylamide; potassium salt | 496 |
| 1-12 | 6-(2-Methoxy-phenyl)-5-methyl-pyridine-3-sulfonic acid 2,4-dichloro-benzoylamide; potassium salt | 451 |
| 1-13 | 6-(2-Methoxy-phenyl)-5-methyl-pyridine-3-sulfonic acid 4-fluoro-2-trifluoromethyl-benzoylamide; potassium salt | 469 |
| 1-14 | 6-(2-Chloro-phenyl)-5-methyl-pyridine-3-sulfonic acid 4-fluoro-2-trifluoromethyl-benzoylamide; potassium salt | 473 |
| 1-15 | 6-(2-Chloro-phenyl)-5-methyl-pyridine-3-sulfonic acid 2-chloro-4-fluoro-benzoylamide; potassium salt | 439 |
| 1-16 | 6-(2-Chloro-phenyl)-5-methyl-pyridine-3-sulfonic acid 4-chloro-2-methoxy-benzoylamide; potassium salt | 451 |

The invention claimed is:

1. A compound according to formula I,

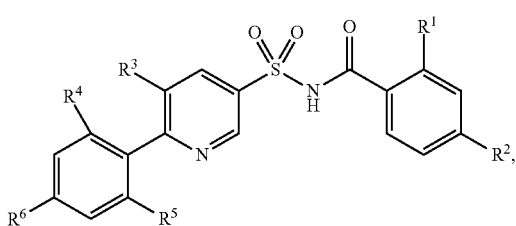

formula I wherein
$R^1$ is selected from the group consisting of: chlorine, bromine, methyl, methoxy and trifluoromethyl;
$R^2$ is selected from the group consisting of: fluorine, chlorine, bromine, methyl and trifluoromethyl;
$R^3$ is selected from the group consisting of: hydrogen and methyl;
$R^4$ is selected from the group consisting of: alkoxy, alkyl, alkylsulfanyl, halogen, trifluoromethyl, trifluoromethoxy, —S(O)$_2$CH$_3$ and —NH—S(O)$_2$CH$_3$;
$R^5$ is selected from the group consisting of: hydrogen, alkoxy, alkyl, halogen, trifluoromethyl and trifluoromethoxy;
$R^6$ is selected from the group consisting of: hydrogen, alkyl and trifluoromethyl;
or a pharmaceutically acceptable salt thereof.

2. A compound according to claim 1, wherein
$R^1$ is selected from the group consisting of: chlorine, methoxy and trifluoromethyl; and
$R^2$ is selected from the group consisting of: fluorine and chlorine.

3. A compound according to claim 1, wherein
$R^1$ is selected from the group consisting of: chlorine, methoxy and trifluoromethyl;
$R^2$ is selected from the group consisting of: fluorine and chlorine;
$R^4$ is selected from the group consisting of: methoxy, methyl, methylsulfanyl, chlorine, trifluoromethyl, —S(O)$_2$CH$_3$ and —NH—S(O)$_2$CH$_3$;
$R^5$ is selected from the group consisting of: hydrogen, methoxy, methyl and fluorine; and
$R^6$ is selected from the group consisting of: hydrogen, methyl and trifluoromethyl.

4. A compound according to claim 1, selected from the group consisting of:
6-(2-Chloro-phenyl)-5-methyl-pyridine-3-sulfonic acid 2-chloro-4-fluoro-benzoylamide; potassium salt;
6-(2,6-Dimethoxy-phenyl)-pyridine-3-sulfonic acid 2-chloro-4-fluoro-benzoylamide;
6-(2-Methoxy-phenyl)-5-methyl-pyridine-3-sulfonic acid 2,4-dichloro-benzoylamide; potassium salt;
6-(2-Fluoro-6-methoxy-phenyl)-pyridine-3-sulfonic acid 2,4-dichloro-benzoylamide; potassium salt;
6-(2,4-Bis-trifluoromethyl-phenyl)-pyridine-3-sulfonic acid 2,4-dichloro-benzoylamide; potassium salt;
6-(2-Methylsulfanyl-phenyl)-pyridine-3-sulfonic acid 2,4-dichloro-benzoylamide; potassium salt;
6-(2,6-Dimethoxy-phenyl)-pyridine-3-sulfonic acid 2,4-dichloro-benzoylamide;
6-(2-Methanesulfonyl-phenyl)-pyridine-3-sulfonic acid 2,4-dichloro-benzoylamide; potassium salt;
6-(2-Chloro-phenyl)-5-methyl-pyridine-3-sulfonic acid 4-chloro-2-methoxy-benzoylamide; potassium salt;
6-(2-Methanesulfonylamino-phenyl)-pyridine-3-sulfonic acid 4-chloro-2-methoxy-benzoylamide; potassium salt;
6-(2,6-Dimethyl-phenyl)-pyridine-3-sulfonic acid 4-chloro-2-methoxy-benzoylamide; potassium salt;
6-(2,4,6-Trimethyl-phenyl)-pyridine-3-sulfonic acid 4-chloro-2-methoxy-benzoylamide; potassium salt;
6-(2,6-Dimethoxy-phenyl)-pyridine-3-sulfonic acid 4-chloro-2-methoxy-benzoylamide; potassium salt;
6-(2-Chloro-phenyl)-5-methyl-pyridine-3-sulfonic acid 4-fluoro-2-trifluoromethyl-benzoylamide; potassium salt;
6-(2-Methoxy-phenyl)-5-methyl-pyridine-3-sulfonic acid 4-fluoro-2-trifluoromethyl-benzoylamide; potassium salt; and
6-(2,6-Dimethoxy-phenyl)-pyridine-3-sulfonic acid 4-fluoro-2-trifluoromethyl-benzoylamide.

5. A pharmaceutical composition comprising a compound according to claim 1 and a pharmaceutically acceptable carrier.

* * * * *